Nov. 26, 1963 A. COBLEY Plant Pat. 2,319
ROSE PLANT
Filed Oct. 9, 1962
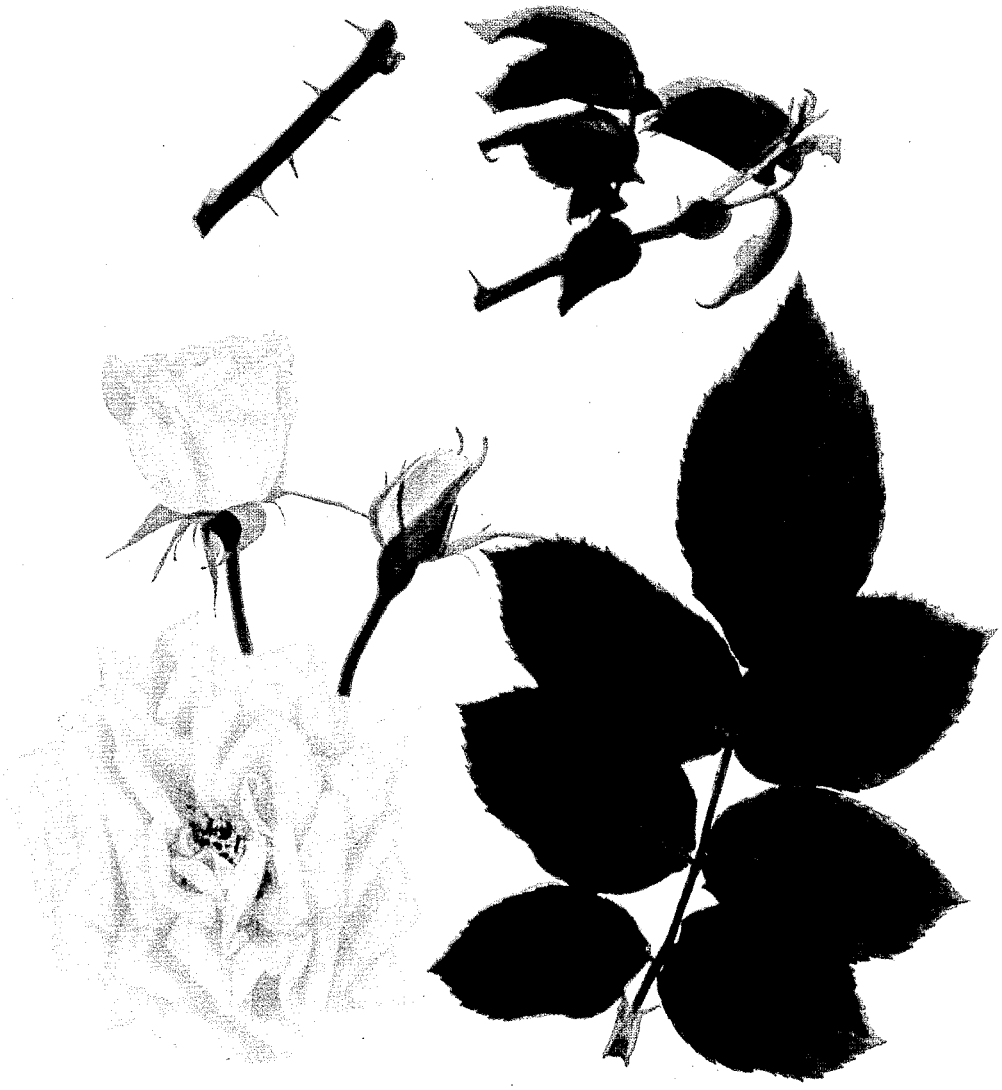
Inventor.
Alfred Cobley
By: Robb & Robb
Attorneys.

United States Patent Office

Plant Pat. 2,319

Patented Nov. 26, 1963

2,319

ROSE PLANT

Alfred Cobley, Earl Shilton, England, assignor to Jackson & Perkins Company, Newark, N.Y., a corporation of New York Filed Oct. 9, 1962, Ser. No. 229,512

1 Claim. (Cl. Plt.—22)

The present invention relates to a new and distinct variety of rose plant of the floribunda class, which was originated by me by crossing the floribunda variety known as "Masquerade" (U.S. Plant Patent No. 975) with the floribunda variety known as "Fashion" (U.S. Plant Patent No. 789).

The primary objective of this breeding was to produce a new rose variety in which there is combined the plant characteristics of the parent variety "Fashion" with the unique flower coloration of the parent variety "Masquerade." This objective was fully achieved, as evidenced by the following unique combination of characteristics which are outstanding in the new variety and which distinguish it from its parents, as well as from all other varieties of which I am aware:

(1) Plant and foliage characteristics which are generally similar to those of the variety "Fashion"; and (2) An attractive and distinctive Flame Scarlet color of the half-open buds, said bud color changing to Bittersweet Orange, very lightly overcast with Salmon-Orange in the open flowers.

Asexual reproduction of my new variety by budding, as performed at Newark, New York, U.S.A., and also at Pleasanton, California, U.S.A., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
- *Seed parent.*—"Masquerade."
- *Pollen parent.*—"Fashion."

Classification:
- *Botanic.*—Floribunda.
- *Commercial.*—Floribunda.

*Flower*

(Observations made from specimens grown in a greenhouse at Newark, New York, U.S.A., in the early afternoon, during the middle of the month of December.)

Blooming habit: Recurrent—continuous.

Bud:
- *Size.*—Medium.
- *Form.*—Ovoid; is not affected by wet or hot weather.
- *Color.*—When sepals first divide—Scarlet, Plate 1. When petals begin to unfurl—Capucine Yellow, Plate 3, lightly overcast with Coral Red, Plate 13. When half-blown: inside of petals—Flame Scarlet, Plate 2; reverse of petals—Capucine Yellow, Plate 3, very lightly overcast on the outer edge of the petals with Bittersweet Orange, Plate 2.
- *Sepals.*—Slightly branched; curl back when petals begin to unfurl. Color: inside—Light Cress Green, Plate 31; outside—Spinach Green, Plate 5.
- *Calyx.*—Color—Spinach Green, Plate 5. Shape—pear. Size—small. Aspect—smooth. Odor when rubbed—none.

- *Peduncle.*—Length — medium. Aspect — prickly. Strength—erect; slender. Color—Forest Green, Plate 17.
- *Opening.*—Opens up well; is not affected by adverse weather conditions.

Bloom:
- *Size.*—Medium. Average size when fully expanded—3½ inches.
- *Borne.*—Both singly and in irregular clusters.
- *Stems.*—Medium length; strong.
- *Form (when first open).*—Cupped. Permanence—retains its form to the end, but outer petals curl back.
- *Petalage.*—Double (full but open center). Number of petals under normal conditions—25.
- *Color.*—Center of flower—Grenadine Red, Plate 2. Outer petals—Mikado Orange, Plate 3, very lightly overcast with Grenadine, Plate 2. Base of petals (aiglet)—Empire Yellow, Plate 4. Inside of petals—Bittersweet Orange, Plate 2, very lightly overcast with Salmon-Orange, Plate 2. Reverse of petals—Pale Yellow-Orange, Plate 3, lightly overcast with Grenadine Pink, Plate 2. General tonality from a distance—Bittersweet Orange, Plate 2, very lightly overcast with Salmon-Orange, Plate 2.
- *Discoloration.*—General tonality at end of first day—Bittersweet Orange, Plate 2, lightly overcast with Salmon-Orange, Plate 2. Second day—Bittersweet Orange, Plate 2, very lightly overcast with Salmon-Orange, Plate 2. Third day—Bittersweet Orange, Plate 2, lightly overcast with Grenadine Pink, Plate 2.

Petals:
- *Texture.*—Leathery; is not affected by wet or hot weather.
- *Appearance.*—Inside—satiny. Outside—shiny.
- *Form.*—Oval.
- *Arrangement.*—Imbricated (regularly arranged shingle-like).
- *Petaloids in center.*—Few; small.
- *Persistence.*—Drop off cleanly.
- *Fragrance.*—Moderate. Nature—tea (average hybrid tea scent).
- *Lasting quality.*—On the plant—long. As cut flower—long.

*Genital Organs*

Stamens, anthers: Medium size; many; regularly arranged around styles. Color—Cadmium Orange, Plate 3.

Stamens, filaments (threads): Medium length. Color—Light Cadmium, Plate 4.

Pollen: Color—Maize Yellow, Plate 4.

Styles: Loosely separated; uneven length; medium length; thin.

Stigmas: Color—Orange Buff, Plate 3.

Ovaries: All enclosed in calyx.

Hips: None.

Seeds: None.

*Plant*

Form: Bush.

Growth: Vigorous; upright.

Foliage: Compound of 5–7 leaflets.
- *Size.*—Medium.
- *Quantity.*—Normal.
- *Color.*—New foliage: upper side—Yellowish Oil Green, Plate 5; under side—Citrine, Plate 4. Old foliage: upper side Spinach Green, Plate 5; under side—Light Bice Green, Plate 17.
- *Shape.*—Oval pointed.
- *Texture.*—Upper side—leathery. Under side—smooth.
- *Ribs and veins.*—Ordinary.

*Edge.*—Serrated (saw-toothed).

*Serration.*—Both double and single; small.

*Leaf stem.*—Color—Madder Brown, Plate 13. Under side—smooth.

*Stipules.*—Short; smooth.

Wood:

*New wood.*—Color—Yellowish Olive, Plate 30. Bark—smooth.

*Old wood.*—Color—Cress Green, Plate 31. Bark—smooth.

Thorns:

*Thorns.*—Quantity; on main stalks from base ordinary; on laterals from stalk—ordinary. Form—narrow base; medium length; hooked downward. Color (when young)—Old Rose, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the floribunda class, substantially as herein shown and described, characterized particularly as to novelty by the unique combination of plant and foliage characteristics generally similar to those of the variety "Fashion" (Plant Patent No. 789), and a distinctive and attractive Flame Scarlet coloration of the half-open buds, said coloration changing to Bittersweet Orange, very lightly overcast with Salmon-Orange in the open flowers.

No references cited.